(12) United States Patent
Eder et al.

(10) Patent No.: US 7,803,156 B2
(45) Date of Patent: Sep. 28, 2010

(54) METHOD AND APPARATUS FOR SURGICAL ELECTROCAUTERY

(75) Inventors: Joseph Eder, Los Altos, CA (US); Benjamin Theodore Nordell, II, San Mateo, CA (US); Peter Seth Edelstein, Menlo Park, CA (US)

(73) Assignee: Aragon Surgical, Inc., Palo Alto, CA (US)

( * ) Notice: Subject to any disclaimer, the term of this patent is extended or adjusted under 35 U.S.C. 154(b) by 770 days.

(21) Appl. No.: 11/371,988

(22) Filed: Mar. 8, 2006

(65) Prior Publication Data

US 2007/0213711 A1 Sep. 13, 2007

(51) Int. Cl.
*A61B 18/18* (2006.01)
(52) U.S. Cl. .......................... 606/51; 606/52
(58) Field of Classification Search .............. 606/51, 606/52, 205–207
See application file for complete search history.

(56) References Cited

U.S. PATENT DOCUMENTS

| | | |
|---|---|---|
| 3,356,408 A | 12/1967 | Stutz |
| 3,845,771 A | 11/1974 | Vise |
| 3,920,021 A | 11/1975 | Hittenbrandt |
| 4,041,952 A | 8/1977 | Morrison et al. |
| 4,492,231 A | 1/1985 | Auth |
| 4,532,924 A | 8/1985 | Auth et al. |
| 4,671,274 A | 6/1987 | Sorochenko |
| 4,972,846 A | 11/1990 | Owens et al. |
| 4,998,527 A | 3/1991 | Meyers |
| 5,037,379 A | 8/1991 | Clayman et al. |
| 5,078,736 A | 1/1992 | Behl |
| 5,151,102 A | 9/1992 | Kamiyama |
| 5,178,618 A | 1/1993 | Kanadarpa |
| 5,190,541 A | 3/1993 | Abele et al. |
| 5,207,691 A | 5/1993 | Nardella |

(Continued)

FOREIGN PATENT DOCUMENTS

CA 2061215 2/1992

(Continued)

OTHER PUBLICATIONS

Abu-Rustum, NR, et al.; *Transperitoneal Laparoscopic Pelvic And Para-Aortic Lymph Node Dissection Using The Argon-Beam Coagulator And Monopolar Instruments: An 8-Year Study And Description Of Technique*; Jun. 2003; Gynecol Oncol. 89 (3): 504-13; Memorial Sloan-Kettering Cancer Center, 1275 York Avenue, New York, NY 10021, USA. gynbreast@mskcc.org.

(Continued)

*Primary Examiner*—Michael Peffley
*Assistant Examiner*—Samantha Good
(74) *Attorney, Agent, or Firm*—Michael A. Glenn; Glenn Patent Group

(57) ABSTRACT

The invention provides a surgical electrocautery method and apparatus that achieves sealing along the entire tissue length, and that also is able to deliver adequate force to produce an effective electrocautery seal. This problem is solved by using an incompressible fluid contained in a sac or sacs positioned to support the one or more electrodes used for electrocauterization. The profile of the electrodes thus conforms to the tissue surface and thickness variations, while exerting an optimized pressure along the entire length of the surface.

14 Claims, 1 Drawing Sheet

U.S. PATENT DOCUMENTS

| | | | |
|---|---|---|---|
| 5,217,030 A | 6/1993 | Yoon | |
| 5,250,074 A * | 10/1993 | Wilk et al. | 606/207 |
| 5,267,998 A | 12/1993 | Hagen | |
| 5,269,780 A | 12/1993 | Roos | |
| 5,269,782 A | 12/1993 | Sutter | |
| 5,273,524 A | 12/1993 | Fox et al. | |
| 5,277,201 A | 1/1994 | Stern | |
| 5,281,216 A | 1/1994 | Klicek | |
| 5,282,799 A | 2/1994 | Rydell | |
| 5,290,287 A | 3/1994 | Boebel et al. | |
| 5,295,990 A | 3/1994 | Levin | |
| 5,300,087 A | 4/1994 | Knoepfler | |
| 5,324,289 A | 6/1994 | Eggers | |
| 5,330,471 A | 7/1994 | Eggers | |
| 5,330,502 A | 7/1994 | Hassler et al. | |
| 5,336,229 A | 8/1994 | Noda | |
| 5,336,237 A | 8/1994 | Chin et al. | |
| 5,341,807 A | 8/1994 | Nardella | |
| 5,342,381 A | 8/1994 | Tidemand | |
| 5,352,223 A | 10/1994 | McBrayer et al. | |
| 5,352,235 A | 10/1994 | Koros et al. | |
| 5,374,277 A | 12/1994 | Hassler et al. | |
| 5,377,415 A | 1/1995 | Gibson | |
| 5,391,166 A | 2/1995 | Eggers | |
| 5,395,369 A | 3/1995 | McBrayer et al. | |
| 5,396,900 A | 3/1995 | Slater et al. | |
| 5,403,312 A | 4/1995 | Yates et al. | |
| 5,417,687 A | 5/1995 | Nardella et al. | |
| 5,423,814 A | 6/1995 | Zhu et al. | |
| 5,443,463 A | 8/1995 | Stern et al. | |
| 5,443,470 A | 8/1995 | Stern et al. | |
| 5,445,638 A | 8/1995 | Rydell et al. | |
| 5,447,513 A | 9/1995 | Davison et al. | |
| 5,449,355 A | 9/1995 | Rhum et al. | |
| 5,456,684 A | 10/1995 | Schmidt et al. | |
| 5,458,598 A | 10/1995 | Feinberg et al. | |
| 5,462,546 A | 10/1995 | Rydell | |
| 5,472,442 A | 12/1995 | Klicek | |
| 5,482,054 A | 1/1996 | Slater et al. | |
| 5,484,435 A | 1/1996 | Fleenor et al. | |
| 5,484,436 A | 1/1996 | Eggers et al. | |
| 5,496,312 A | 3/1996 | Klicek | |
| 5,496,317 A | 3/1996 | Goble et al. | |
| 5,514,134 A | 5/1996 | Rydell et al. | |
| 5,531,744 A | 7/1996 | Nardella et al. | |
| 5,540,684 A | 7/1996 | Hassler, Jr. | |
| 5,540,685 A | 7/1996 | Parins et al. | |
| 5,542,945 A | 8/1996 | Fritzsch | |
| 5,549,606 A | 8/1996 | McBrayer et al. | |
| 5,549,637 A | 8/1996 | Crainich | |
| 5,556,397 A | 9/1996 | Long et al. | |
| 5,558,100 A | 9/1996 | Cox | |
| 5,558,671 A | 9/1996 | Yates | |
| 5,562,700 A | 10/1996 | Huitema et al. | |
| 5,562,701 A | 10/1996 | Huitema et al. | |
| 5,562,702 A | 10/1996 | Huitema et al. | |
| 5,562,720 A | 10/1996 | Stern et al. | |
| 5,564,615 A | 10/1996 | Bishop et al. | |
| 5,569,243 A | 10/1996 | Kortenbach | |
| 5,571,100 A | 11/1996 | Goble et al. | |
| 5,573,535 A | 11/1996 | Viklund | |
| 5,578,052 A | 11/1996 | Koros et al. | |
| 5,599,350 A | 2/1997 | Schulze et al. | |
| 5,601,224 A | 2/1997 | Bishop et al. | |
| 5,603,700 A | 2/1997 | Daneshvar | |
| 5,611,803 A | 3/1997 | Heaven | |
| 5,624,452 A | 4/1997 | Yates | |
| 5,637,110 A | 6/1997 | Pennybacker | |
| 5,637,111 A | 6/1997 | Sutcu et al. | |
| 5,653,692 A | 8/1997 | Masterson et al. | |
| 5,658,281 A | 8/1997 | Heard | |
| 5,662,662 A | 9/1997 | Bishop et al. | |
| 5,665,085 A | 9/1997 | Nardella | |
| 5,665,100 A | 9/1997 | Yoon | |
| 5,667,526 A | 9/1997 | Levin | |
| 5,669,907 A | 9/1997 | Platt et al. | |
| 5,673,840 A | 10/1997 | Schulze et al. | |
| 5,673,841 A | 10/1997 | Schulze et al. | |
| 5,674,184 A | 10/1997 | Hassler, Jr. | |
| 5,674,220 A | 10/1997 | Fox et al. | |
| 5,680,982 A | 10/1997 | Schulze et al. | |
| 5,681,282 A | 10/1997 | Eggers et al. | |
| 5,683,385 A | 11/1997 | Kortenbach | |
| 5,683,388 A | 11/1997 | Slater | |
| 5,688,270 A | 11/1997 | Yates et al. | |
| 5,693,051 A | 12/1997 | Schulze et al. | |
| 5,697,949 A | 12/1997 | Guirtino et al. | |
| 5,700,261 A | 12/1997 | Brikerhoff | |
| 5,702,390 A | 12/1997 | Austin et al. | |
| 5,704,534 A | 1/1998 | Huitema et al. | |
| 5,707,369 A | 1/1998 | Vatekunas et al. | |
| 5,709,680 A | 1/1998 | Yates et al. | |
| 5,713,896 A | 2/1998 | Nardella et al. | |
| 5,715,832 A | 2/1998 | Koblish et al. | |
| 5,718,703 A | 2/1998 | Chin | |
| 5,728,143 A | 3/1998 | Gough et al. | |
| 5,733,283 A | 3/1998 | Malis et al. | |
| 5,735,289 A | 4/1998 | Pfeffer et al. | |
| 5,735,848 A | 4/1998 | Yates et al. | |
| 5,735,849 A | 4/1998 | Baden et al. | |
| 5,741,285 A | 4/1998 | McBrayer | |
| 5,743,906 A | 4/1998 | Parins et al. | |
| 5,755,717 A | 5/1998 | Yates et al. | |
| 5,769,849 A | 6/1998 | Eggers | |
| 5,776,130 A | 7/1998 | Buysse et al. | |
| 5,797,906 A | 8/1998 | Rhum et al. | |
| 5,810,811 A | 9/1998 | Yates et al. | |
| 5,817,092 A | 10/1998 | Behl | |
| 5,823,066 A | 10/1998 | Huitema et al. | |
| 5,833,689 A | 11/1998 | Long | |
| 5,833,690 A | 11/1998 | Yates et al. | |
| 5,855,576 A | 1/1999 | LeVeen et al. | |
| 5,860,975 A | 1/1999 | Goble et al. | |
| 5,891,142 A | 4/1999 | Eggers et al. | |
| 5,954,720 A | 9/1999 | Wilson et al. | |
| 6,003,517 A | 12/1999 | Sheffield et al. | |
| 6,004,319 A | 12/1999 | Goble et al. | |
| 6,030,384 A | 2/2000 | Nezhat | |
| 6,050,995 A | 4/2000 | Durgin | |
| 6,056,744 A | 5/2000 | Edwards | |
| 6,056,746 A | 5/2000 | Goble et al. | |
| 6,066,139 A | 5/2000 | Ryan et al. | |
| 6,068,626 A | 5/2000 | Harrington et al. | |
| 6,074,386 A | 6/2000 | Goble et al. | |
| 6,086,586 A | 7/2000 | Hooven | |
| 6,090,106 A | 7/2000 | Goble et al. | |
| 6,093,186 A | 7/2000 | Goble | |
| 6,096,037 A | 8/2000 | Mulier et al. | |
| 6,099,550 A | 8/2000 | Yoon | |
| 6,123,701 A | 9/2000 | Nezhat | |
| 6,152,920 A | 11/2000 | Thompson et al. | |
| 6,162,220 A | 12/2000 | Nezhat | |
| 6,174,309 B1 | 1/2001 | Wrublewski et al. | |
| 6,179,832 B1 | 1/2001 | Jones et al. | |
| 6,203,541 B1 | 3/2001 | Kappel | |
| 6,206,877 B1 | 3/2001 | Kese et al. | |
| 6,228,084 B1 | 5/2001 | Kirwan, Jr. | |
| 6,277,114 B1 | 8/2001 | Bullivant et al. | |
| 6,283,963 B1 | 9/2001 | Regula | |
| 6,287,304 B1 | 9/2001 | Eggers et al. | |
| 6,293,946 B1 | 9/2001 | Thorne | |
| 6,306,134 B1 | 10/2001 | Goble et al. | |
| 6,312,430 B1 | 11/2001 | Wilson et al. | |
| 6,322,494 B1 | 11/2001 | Bullivant et al. | |

| Patent No. | Date | Inventor |
|---|---|---|
| 6,361,559 B1 | 3/2002 | Hauser et al. |
| 6,364,879 B1 | 4/2002 | Chen et al. |
| 6,371,956 B1 | 4/2002 | Wilson et al. |
| 6,391,029 B1 | 5/2002 | Hooven et al. |
| 6,398,779 B1 | 6/2002 | Buysse et al. |
| 6,416,509 B1 | 7/2002 | Goble et al. |
| 6,440,130 B1 | 8/2002 | Mulier et al. |
| 6,443,952 B1 | 9/2002 | Mulier et al. |
| 6,464,702 B2 | 10/2002 | Schulze et al. |
| 6,485,486 B1 | 11/2002 | Trembly et al. |
| 6,485,489 B2 * | 11/2002 | Teirstein et al. ............... 606/41 |
| 6,491,690 B1 | 12/2002 | Goble et al. |
| 6,494,881 B1 | 12/2002 | Bales et al. |
| 6,514,252 B2 | 2/2003 | Nezhat et al. |
| 6,517,530 B1 | 2/2003 | Kleven |
| 6,520,185 B1 | 2/2003 | Bommannan et al. |
| 6,533,784 B2 | 3/2003 | Truckai et al. |
| 6,554,829 B2 | 4/2003 | Schulze et al. |
| 6,564,806 B1 | 5/2003 | Fogarty et al. |
| 6,565,560 B1 | 5/2003 | Goble et al. |
| 6,565,561 B1 | 5/2003 | Goble et al. |
| 6,584,360 B2 | 6/2003 | Francischelli |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,659 B1 | 9/2003 | de la Torre et al. |
| 6,623,482 B2 | 9/2003 | Pendekanti et al. |
| 6,626,901 B1 | 9/2003 | Treat et al. |
| 6,645,198 B1 | 11/2003 | Bommannan et al. |
| 6,645,201 B1 | 11/2003 | Utley et al. |
| 6,648,839 B2 | 11/2003 | Manna |
| 6,652,518 B2 | 11/2003 | Wellman |
| 6,656,177 B2 | 12/2003 | Truckai et al. |
| 6,676,660 B2 | 1/2004 | Wampler et al. |
| 6,682,526 B1 | 1/2004 | Jones et al. |
| 6,682,527 B2 | 1/2004 | Strul |
| 6,695,840 B2 | 2/2004 | Schulze |
| 6,722,371 B1 | 4/2004 | Fogarty et al. |
| 6,726,682 B2 | 4/2004 | Harrington et al. |
| 6,736,814 B2 | 5/2004 | Manna et al. |
| 6,743,229 B2 | 6/2004 | Buysse et al. |
| 6,752,154 B2 | 6/2004 | Fogarty et al. |
| 6,752,803 B2 | 6/2004 | Goldman et al. |
| 6,755,827 B2 | 6/2004 | Mulier et al. |
| 6,770,070 B1 | 8/2004 | Balbierz |
| 6,773,435 B2 | 8/2004 | Schulze et al. |
| 6,776,780 B2 | 8/2004 | Mulier et al. |
| 6,808,525 B2 | 10/2004 | Latterell et al. |
| 6,821,273 B2 | 11/2004 | Mollenauer |
| 6,837,888 B2 | 1/2005 | Ciarrocca et al. |
| 6,840,938 B1 | 1/2005 | Morley et al. |
| 6,843,789 B2 | 1/2005 | Goble |
| 6,852,108 B2 | 2/2005 | Barry et al. |
| 6,858,028 B2 | 2/2005 | Mulier et al. |
| 6,889,089 B2 | 5/2005 | Behl et al. |
| 6,893,435 B2 | 5/2005 | Goble |
| 6,896,673 B2 | 5/2005 | Hooven |
| 6,902,536 B2 | 6/2005 | Manna et al. |
| 6,908,463 B2 | 6/2005 | Treat et al. |
| 6,913,579 B2 | 7/2005 | Truckai et al. |
| 6,918,909 B2 | 7/2005 | Kelly et al. |
| 6,923,803 B2 | 8/2005 | Goble |
| 6,923,806 B2 | 8/2005 | Hooven et al. |
| 6,929,642 B2 | 8/2005 | Xiao et al. |
| 6,936,048 B2 | 8/2005 | Hurst |
| 6,953,461 B2 | 10/2005 | McClurken et al. |
| 6,981,628 B2 | 1/2006 | Wales |
| 7,063,699 B2 | 6/2006 | Hess et al. |
| 7,090,637 B2 | 8/2006 | Danitz et al. |
| 7,090,673 B2 | 8/2006 | Dycus et al. |
| 7,090,685 B2 | 8/2006 | Kortenbach et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,118,587 B2 | 10/2006 | Dycus et al. |
| 7,125,409 B2 | 10/2006 | Truckai et al. |
| 7,250,048 B2 | 7/2007 | Francischelli et al. |
| 7,255,697 B2 | 8/2007 | Dycus et al. |
| 7,267,677 B2 | 9/2007 | Johnson et al. |
| 7,270,664 B2 | 9/2007 | Johnson et al. |
| 7,276,068 B2 | 10/2007 | Johnson et al. |
| 7,278,991 B2 | 10/2007 | Morris et al. |
| 7,291,143 B2 | 11/2007 | Swanson |
| 7,329,256 B2 | 2/2008 | Johnson et al. |
| 7,364,577 B2 | 4/2008 | Wham et al. |
| 7,367,972 B2 | 5/2008 | Francischelli et al. |
| 7,410,483 B2 | 8/2008 | Danitz et al. |
| 7,513,898 B2 | 4/2009 | Johnson et al. |
| 7,540,872 B2 | 6/2009 | Schechter et al. |
| 7,588,566 B2 | 9/2009 | Treat et al. |
| 2001/0029367 A1 | 10/2001 | Fleenor et al. |
| 2002/0107514 A1 | 8/2002 | Hooven |
| 2002/0128643 A1 | 9/2002 | Simpson et al. |
| 2002/0151882 A1 | 10/2002 | Marko et al. |
| 2002/0183738 A1 * | 12/2002 | Chee et al. ..................... 606/41 |
| 2003/0018331 A1 | 1/2003 | Dycus et al. |
| 2003/0078577 A1 * | 4/2003 | Truckai et al. ................. 606/51 |
| 2003/0158547 A1 * | 8/2003 | Phan ........................... 606/41 |
| 2003/0199869 A1 | 10/2003 | Johnson et al. |
| 2003/0229344 A1 | 12/2003 | Dycus et al. |
| 2004/0049185 A1 | 3/2004 | Latterell et al. |
| 2004/0068274 A1 | 4/2004 | Hooven |
| 2004/0097919 A1 | 5/2004 | Wellman et al. |
| 2004/0122423 A1 | 6/2004 | Dycus et al. |
| 2004/0236320 A1 | 11/2004 | Protsenko |
| 2004/0236326 A1 | 11/2004 | Schulze |
| 2005/0010212 A1 | 1/2005 | McClurken et al. |
| 2005/0015085 A1 | 1/2005 | McClurken et al. |
| 2005/0021024 A1 | 1/2005 | Hooven |
| 2005/0021026 A1 | 1/2005 | Baily |
| 2005/0033277 A1 | 2/2005 | Clague et al. |
| 2005/0033278 A1 | 2/2005 | McClurken et al. |
| 2005/0033282 A1 | 2/2005 | Hooven |
| 2005/0070895 A1 | 3/2005 | Ryan et al. |
| 2005/0070978 A1 | 3/2005 | Bek et al. |
| 2005/0090819 A1 | 4/2005 | Goble |
| 2005/0107781 A1 | 5/2005 | Ostrovsky et al. |
| 2005/0113820 A1 | 5/2005 | Goble et al. |
| 2005/0113826 A1 | 5/2005 | Johnson et al. |
| 2005/0119654 A1 | 6/2005 | Swanson et al. |
| 2005/0131390 A1 | 6/2005 | Heinrich et al. |
| 2005/0137591 A1 | 6/2005 | Barry et al. |
| 2005/0171530 A1 | 8/2005 | Hooven |
| 2005/0171533 A1 | 8/2005 | Latterell et al. |
| 2005/0187561 A1 | 8/2005 | Lee-Sepsick et al. |
| 2005/0192568 A1 | 9/2005 | Truckai et al. |
| 2005/0192633 A1 | 9/2005 | Montpetit |
| 2005/0203500 A1 | 9/2005 | Saadat et al. |
| 2005/0256522 A1 | 11/2005 | Franciscelli et al. |
| 2006/0025812 A1 | 2/2006 | Shelton |
| 2006/0041254 A1 | 2/2006 | Francischelli et al. |
| 2006/0052778 A1 | 3/2006 | Chapman et al. |
| 2006/0064085 A1 | 3/2006 | Schechter et al. |
| 2006/0142751 A1 | 6/2006 | Treat et al. |
| 2006/0167451 A1 | 7/2006 | Crooper |
| 2006/0189980 A1 | 8/2006 | Johnson et al. |
| 2006/0190029 A1 | 8/2006 | Wales |
| 2006/0199999 A1 | 9/2006 | Ikeda et al. |
| 2006/0217709 A1 | 9/2006 | Couture et al. |
| 2006/0226196 A1 | 10/2006 | Hueil et al. |
| 2006/0229665 A1 | 10/2006 | Wales et al. |
| 2006/0258954 A1 | 11/2006 | Timberlake et al. |
| 2006/0259035 A1 | 11/2006 | Nezhat |
| 2006/0271038 A1 | 11/2006 | Johnson et al. |
| 2006/0271042 A1 | 11/2006 | Latterell et al. |
| 2006/0287674 A1 | 12/2006 | Ginn et al. |

| | | | | | |
|---|---|---|---|---|---|
| 2006/0289602 A1 | 12/2006 | Wales et al. | EP | 2065006 | 6/2009 |
| 2007/0055231 A1 | 3/2007 | Dycus et al. | EP | 2106764 | 10/2009 |
| 2007/0062017 A1 | 3/2007 | Dycus et al. | EP | 2110093 | 10/2009 |
| 2007/0073340 A1 | 3/2007 | Shelton et al. | JP | 11070123 | 3/1999 |
| 2007/0129726 A1 | 6/2007 | Eder et al. | JP | 11070124 | 3/1999 |
| 2007/0179497 A1 | 8/2007 | Eggers et al. | JP | 2003/088534 | 3/2003 |
| 2007/0208330 A1 | 9/2007 | Treat et al. | JP | 2004/049566 | 2/2004 |
| 2007/0250113 A1 | 10/2007 | Hegeman et al. | JP | 2005/021703 | 1/2005 |
| 2007/0260242 A1 | 11/2007 | Dycus et al. | JP | 2005/144193 | 6/2005 |
| 2007/0299439 A1 | 12/2007 | Latterell et al. | WO | WO 92/22257 | 12/1992 |
| 2008/0039835 A1 | 2/2008 | Johnson et al. | WO | WO 93/08754 | 5/1993 |
| 2008/0045947 A1 | 2/2008 | Johnson et al. | WO | WO 94/00060 | 1/1994 |
| 2008/0114356 A1 | 5/2008 | Johnson et al. | WO | WO 95/02371 | 1/1995 |
| 2008/0188844 A1 | 8/2008 | McGreevy et al. | WO | WO 95/14436 | 6/1995 |
| 2008/0195093 A1 | 8/2008 | Couture et al. | WO | WO 95/25471 | 9/1995 |
| 2008/0275446 A1 | 11/2008 | Messerly | WO | WO 96/05776 | 2/1996 |
| 2009/0018535 A1 | 1/2009 | Schechter et al. | WO | WO9616605 | 6/1996 |
| 2009/0138006 A1 | 5/2009 | Bales et al. | WO | WO 96/23449 | 8/1996 |
| 2009/0149853 A1 | 6/2009 | Shields et al. | WO | WO 97/24073 | 7/1997 |
| 2009/0171354 A1 | 7/2009 | Deville et al. | WO | WO 97/24074 | 7/1997 |
| 2009/0234347 A1 | 9/2009 | Treat et al. | WO | WO 97/24995 | 7/1997 |
| 2009/0240245 A1 | 9/2009 | Deville et al. | WO | WO 98/12999 | 4/1998 |
| 2009/0299367 A1 | 12/2009 | Ginnebaugh et al. | WO | WO 98/43548 | 10/1998 |

FOREIGN PATENT DOCUMENTS

| | | |
|---|---|---|
| EP | 487269 | 5/1991 |
| EP | 440385 | 7/1991 |
| EP | 502268 | 9/1992 |
| EP | 562195 | 9/1993 |
| EP | 658333 | 6/1995 |
| EP | 536998 | 4/1996 |
| EP | 518230 | 5/1996 |
| EP | 0737446 | 10/1996 |
| EP | 875209 | 4/1998 |
| EP | 878169 | 11/1998 |
| EP | 640315 | 12/1998 |
| EP | 923907 | 6/1999 |
| EP | 640317 | 9/1999 |
| EP | 771176 | 7/2000 |
| EP | 1050278 | 11/2000 |
| EP | 1064886 | 1/2001 |
| EP | 833593 | 2/2001 |
| EP | 1254637 | 11/2002 |
| EP | 1293169 | 3/2003 |
| EP | 1293170 | 3/2003 |
| EP | 869742 | 5/2003 |
| EP | 1330989 | 7/2003 |
| EP | 1330991 | 7/2003 |
| EP | 1344498 | 9/2003 |
| EP | 873089 | 10/2003 |
| EP | 742696 | 11/2003 |
| EP | 959784 | 4/2004 |
| EP | 0794735 | 7/2004 |
| EP | 1004277 | 7/2004 |
| EP | 959786 | 9/2004 |
| EP | 913126 | 10/2004 |
| EP | 956827 | 10/2004 |
| EP | 1472984 | 11/2004 |
| EP | 1025807 | 12/2004 |
| EP | 1486177 | 12/2004 |
| EP | 1518498 | 3/2005 |
| EP | 1518499 | 3/2005 |
| EP | 927543 | 4/2005 |
| EP | 1532933 | 5/2005 |
| EP | 1621146 | 2/2006 |
| EP | 1632192 | 3/2006 |
| EP | 1637086 | 3/2006 |
| EP | 1645237 | 4/2006 |
| EP | 1747761 | 1/2007 |
| EP | 1852081 | 11/2007 |
| EP | 1862138 | 12/2007 |
| EP | 1958583 | 8/2008 |
| WO | WO 98/53750 | 12/1998 |
| WO | WO 99/23933 | 5/1999 |
| WO | WO 99/51155 | 10/1999 |
| WO | WO 99/51158 | 10/1999 |
| WO | WO 99/52459 | 10/1999 |
| WO | WO 99/56646 | 11/1999 |
| WO | WO 00/13192 | 3/2000 |
| WO | WO 00/13193 | 3/2000 |
| WO | WO 00/47124 | 8/2000 |
| WO | WO0112090 | 2/2001 |
| WO | WO 01/35846 | 5/2001 |
| WO | WO 01/54602 | 8/2001 |
| WO | WO 01/58372 | 8/2001 |
| WO | WO 01/82812 | 11/2001 |
| WO | WO 02/24092 | 3/2002 |
| WO | WO 02/36028 | 5/2002 |
| WO | WO 02/067798 | 7/2002 |
| WO | WO 02/058542 | 8/2002 |
| WO | WO 02/071926 | 9/2002 |
| WO | WO 03/024348 | 3/2003 |
| WO | WO 03/096886 | 11/2003 |
| WO | WO 03/103522 | 12/2003 |
| WO | WO2004032596 | 4/2004 |
| WO | WO2004073490 | 9/2004 |
| WO | WO 2004/098383 | 11/2004 |
| WO | WO 2004/103156 | 12/2004 |
| WO | WO 2005/009213 | 2/2005 |
| WO | WO 2005/034729 | 4/2005 |
| WO | WO 2005/079901 | 9/2005 |
| WO | WO 2005/115251 | 12/2005 |
| WO | WO 2006/124601 | 11/2006 |
| WO | WO2006124518 | 11/2006 |
| WO | WO2008094564 | 8/2008 |
| WO | WO2009070780 | 6/2009 |
| WO | WO2009154976 | 12/2009 |

OTHER PUBLICATIONS

Aoki, T. et al.; *Thoracoscopic Resection Of The Lung With The Ultrasonic Scalpel*; Apr. 1999 Ann Thorac Surg.; 67 (4): 1181-3; Department of Thoracic Surgery, Saiseikai Kanagawaken Hospital, Yokohama, Japan.

*Arthrocare Receives Clearance To Market Coblation-Based Devices For Gynecology And Laparoscopic Surgery; Clearance Includes Plasma Forceps And 21 Specific Indications*; Oct. 25, 2001; Business Wire, p. 0524.

Bergamaschi, R. et al.; *Laparoscopic Intracorporeal Bowel Resection With Ultrasound Versus Electrosurgical Dissection*; Jan.-Mar.

2001; JSLS. 5 (1): 17-20; National Center for Advanced Laparoscopic Surgery, Tondheim, Norway. r.bergamaschi@altavista.net.

Berguer, Ramon et al.; *SAGES 2001 Hands-On Course I- Taking It To The Next Level: Advanced Laparoscopic Techniques*; http://www.sages.org/01program/syllabi/ho1/ho1.html#schirme.

Briani, S. et al.; *Pseudo-Bipolar Electrocoagulation With A Branched Forceps*; 1967; Minerva Neurochir.; 11 (3): 306-11.

Cakan, A. et al.; *The Histological Effect Of Harmonic Scalpel And Electrocautery In Lung Resections. An Experimental Study In A Rat Model*; Feb. 2004; J Cardiovasc Surg (Torino).; 45 (1): 63-5; Department of Thoracic Surgery, Ege University School of Medicine, Izmir, Turkey. alpcakan@gohip.com.

Ceviker, N. et al.; *A New Coated Bipolar Coagulator: Technical Note*; 1998; Acta Neurochir (Wien).; 140 (6): 619-20; Department of Neurosurgery, Faculty of Medicine, Gazi University, Ankara, Turkey.

Cherchi, PL, et al.; *Utility Of Bipolar Electrocautery Scissors For Cervical Conization*; 2002; Eur J Gynaecol Oncol. 2002; 23 (2): 154-6; Department of Pharmacology, Gynecology and Obstetrics, University of Sassari, Italy.

*Circon Corporation—Company Report*; Investext, p. 1-13; Jan. 3, 1995.

Colvin, D.P. et al.; *Development Of An Endoscopic RF Hyperthermia System For Deep Tumor Therapy*; 1987; American Society of Mechanical Engineers, Heat Transfer Division, (Publication) HTD v. 95. Publ by ASME (BED-v 7), New York, NY, USA p. 25-30.

Corson, S.L.; *Two New Laparoscopic Instruments: Bipolar Sterilizing Forceps And Uterine Manipulator*; Jan.-Feb. 1977; Medical Instrumentation vol. 11, No. 1 p. 7-8;; USA.

*Curon Medical Announces Presentation Of Positive Clinical Study Results Of Stretta(R) Procedure For Gastroesophageal Reflux Disease (GERD)*; Mar. 20, 2002; PR Newswire, pNYW07920032002.

*Curon Announces The Publication Of Data Supporting Durability And Effectiveness Of Stretta (R) System;—Positive One Year Follow-Up Data Of U.S. Clinical Trial Published In Gastrointestinal Endoscopy*; Feb. 7, 2002; PR Newswire, pNYTH10307022002.

Daniel, P. et al.; *Ultrasonic Sealing Of The Lung Parenchyma After Atypical Resection; Z Exp Chir Transplant Kunstliche Organe*. 1987; 20 (2): 117-21.

Digeronimo, EM et al.; *Cut-Blot-Coagulate: A New Time Saving Device*; Nov. 1982 Plast Reconstr Surg.; 70 (5): 639-40.

Dubuc-Lissoir, J.; *Use Of A New Energy-Based Vessel Ligation Device During Laparoscopic Gynecologic Oncologic Surgery*; Mar. 2003 Surg Endosc.; 17 (3): 466-8. Epub Oct. 31, 2002; Department of Obstetrics and Gynecology, CHUM—Notre-Dame Hospital, Pavillon Charles-Simard, 2065 Alexandre-de-Seve, 4th Floor, Montreal, Quebec, Canada, H2L 2W5. josee.dubuc-lissoir.chum@ssss.gouv.qc.ca.

Eichfeld U., et al.; *Evaluation Of Ultracision In Lung Metastatic Surgery*; Oct. 2000 Ann Thorac Surg.; 70 (4): 1181-4; Department of Surgery I, General Surgery, Surgical Oncology and Thoracic Surgery, and Institute of Pathology, University of Leipzig, Germany. eichu@medizin.uni-leipzig.de.

*Enable Medical Introduces Second Generation Bipolar Scissors*; Dec. 1998; Health Industry Today, pNA.

Ercoli, A. et al.; *Radiofrequency Bipolar Coagulation For Radical Hysterectomy: Technique, Feasibility And Complications*; Mar.-Apr. 2003 Int J Gynecol Cancer.; 13 (2): 187-91;Department of Obstetrics and Gynecology, Catholic University, Rome, Italy.

*Everest Medical Announces Introduction Of 3mm Bipolar Forceps*; Oct. 2, 1996; PR Newswire, p1002MNW021.

*Everest Medical Discusses Patent Status; Forecasts $1 Million Revenue First Quarter; Introduces Next Generation Bipolar Scissors*; Mar. 31, 1994; PR Newswire, pN/A.

*Everest Medical Introduces New Quadripolar (TM) Cutting Forceps At The Global Congress Of Gynecologic Endoscopy Meeting*; Nov. 8, 1999; PR Newswire p. 8927.

*Everest Medical Releases Bicoag (TM) For Use In Treating Bleeding Ulcers*; May 9, 1990; News Release, p. 1.

*Everest Medical Reports Record First Quarter Results; Introduces Next Generation Bipolar Scissors*; Apr. 19, 1994; PR Newswire, pN/A.

Forestier D. et al.; *Do Bipolar Scissors Increase Postoperative Adhesions? An Experimental Double-Blind Randomized Trial*; Nov. 2002 Ann Chir.; 127 (9): 680-4; Service de chirurgie generale et digestive, Hotel-Dieu, boulevard Leon-Malfreyt, 63058 Clermont-Ferrand, France.

Gerasin VA et al.; *Endoscopic Electrosurgery Of The Trachea And Bronchi*; Sep.-Oct. 1988 Grudn Khir.; (5): 50-3.

Gyr, T. et al.; *Minimal Invasive Laparoscopic Hysterectomy With Ultrasonic Scalpel*; Jun. 2001 Am J Surg.; 181 (6): 516-9; Department of Obstetrics and Gynecology, Regional Hospital, Lugano, Switzerland.

Harrell, AG et al.; *Energy Sources In Laparoscopy*; Sep. 2004 Semin Laparosc Surg.; 11 (3): 201-9; Carolinas Laparoscopic and Advanced Surgery Program, Carolinas Medical Center, Charlotte, NC 28203, USA.

Hayashi A. et al.; *Experimental And Clinical Evaluation Of The Harmonic Scalpel In Thoracic Surgery*; 1999; Kurume Med J.; 46 (1): 25-9; Department of Surgery, Kurume University School of Medicine, Japan.

Hefni, MA et al.; *Safety And Efficacy Of Using The Ligasure Vessel Sealing System For Securing The Pedicles In Vaginal Hysterectomy: Randomised Controlled Trial*; BJOG. Mar. 2005; 112 (3): 329-33; Department of Gynecology, Benenden Hospital, Kent TN17 7AX, UK.

Heniford BT et al.; *Initial Results With An Electrothermal Bipolar Vessel Sealer*; Aug. 2001 Surg Endosc.; 15 (8): 799-801. Epub May 14, 2001; Carolinas Laparoscopic and Advanced Surgery Program, Department of General Surgery, Carolinas Medical Center, 1000 Blythe Boulevard, MEB # 601, Charlotte, NC, USA.

Kamat, AA et al.; *Superiority Of Electrocautery Over The Suture Method For Achieving Cervical Cone Bed Hemostasis*; Oct. 2003 Obstet Gynecol.; 102 (4): 726-30; Department of Obstetrics and Gynecology, Baylor College of Medicine, Houston, Texas 77030, USA. akamat@bcm.tmc.edu.

Kato, K. et al.; *A Computer Based, Temperature Controlled Bipolar Electrocoagulation System*; Sep. 1996 Eur J Obstet Gynecol Reprod Biol.; 68 (1-2): 119-22; Department of Obstetrics and Gynecology, University of Essen, Germany.

Kennedy, JS et al.; *High-Burst-Strength, Feedback-Controlled Bipolar Vessel Sealing*; Jun. 1998 Surg Endosc.; 12 (6): 876-8; Valleylab, Inc., 5920 Longbow Drive, Boulder, CO 80301, USA.

Kim, Byungkyu et al.; *Design And Fabrication Of A Locomotive Mechanism For Capsule-Type Endoscopes Using Shape Memory Alloys (Smas)*; Feb. 2005. IEEE/ASME Transactions on Mechatronics, vol. 10, No. 1, p. 77-86; USA.

Koch, C. et al.; *Determination Of Temperature Elevation In Tissue During The Application Of The Harmonic Scalpel*; Feb. 2003 Ultrasound Med Biol.; 29 (2): 301-9; Ultrasonics Section, Physikalisch-Technische Bundesanstalt Braunschweig, Braunschweig, Germany. christian.koch@ptb.de.

Kohler C. et al.; *Laparoscopic Coagulation Of The Uterine Blood Supply In Laparoscopic-Assisted Vaginal Hysterectomy Is Associated With Less Blood Loss*; 2004 Eur J Gynaecol Oncol.; 25 (4): 453-6; Department of Gynecology, Friedrich Schiller University, Jena, Germany.

Kung, RC et al; *A New Bipolar System for Performing Operative Hysetroscopy In Normal Saline*; Aug. 1999; 6 (3): 331-6J Am Assoc Gynecol Laparosc. http://www.ncbi.nlm.nih.gov/entrez/query.fcgi?cmd=Retrieve&db=pubmed&dopt=Abstract&list_uids=10459037&query_hl=1.

Kwok, A. et al.; *Comparison Of Tissue Injury Between Laparosonic Coagulating Shears And Electrosurgical Scissors In The Sheep Model*; Aug. 2001 J Am Assoc Gynecol Laparosc.; 8 (3): 378-84; Department of Endosurgery, Women's Institute, University of Sydney, Australia.

Landman J. et al.; *Evaluation Of A Vessel Sealing System, Bipolar Electrosurgery, Harmonic Scalpel, Titanium Clips, Endoscopic Gastrointestinal Anastomosis Vascular Staples And Sutures For Arterial And Venous Ligation In A Porcine Model*; Feb. 2003 J Urol.; 169 (2): 697-700; Department of Surgery (Division of Urology), Washington University School of Medicine, St. Louis, Missouri, USA.

Lantis, JC II et al.; *Comparison Of Coagulation Modalities In Surgery*; Dec. 1998 J Laparoendosc Adv Surg Tech A.; 8 (6): 381-94; Surgical Research Laboratory, New England Medical Center, Boston, Massachusetts, USA.

*Laparoscopic Lasers vs. Electrosurgery: Debated Technology Choices*; Jun. 6, 1991; The BBI Newsletter, v.14, n. 6, p. N/A.

Levy, Barbara et al.; *Update On Hysterectomy: New Technologies And Techniques*; Feb. 2003; http://www.obgmanagement.com/supplements/pdf/hysterectomy.pdf; A supplement to OBG Management.

Levy, Barbara; *Use Of A New Vessel Ligation Device During Vaginal Hysterectomy*; As presented at FIGO 2000, Washington, D.C.; University of Washington School of Medicine; Federal Way, Washington, USA; © 2000 Valleylab.

Lin, J. et al.; *Application Of Ultrasonic Scalpel In Gynecologic Operative Laparoscopy*; Dec. 2001 Chin Med J (Engl.); 114 (12): 1283-5; Department of Gynecology, Women's Hospital, Medical School of Zhejiang University, Hangzhou 310006, China. Zuying@mail.hz.zj.cn.

Lyons, TL et al.; *An Innovative Bipolar Instrument For Laparoscopic Surgery*; JSLS. Jan.-Mar. 2005; 9 (1): 39-41; Center for Women's Care & Reproductive Surgery, Atlanta, Georgia, USA cwcrs@mindspring.com.

*Market And Technology Updates: Bipolar Endoscopic Device*; Jan. 24, 1990; The BBI Newsletter, v.13, n.1, pN/A.

Matsumura Y. et al.; *New Surgical Technique Of Pulmonary Segmentectomy By Ultrasonic Scalpel And Absorbable Sealing Materials*; Jan. 2004 Kyobu Geka.; 57 (1): 31-7; Department of Thoracic Surgery, Institute of Development, Aging and Cancer, Tohoku University, Sendai, Japan.

Mundt, C. et al.; *Advanced Sensor Systems For Improved Labor And Fetal Monitoring*; 1998; ISA TECH/EXPO Technology Update Conference Proceedings v. 2 n. 2, p. 79-89; 1998.

Nikolov, N. et al.; *Remote Controllable Vessel Occlusion Device*; Jan. 1978 Med Biol Eng Comput.; 16 (1): 116-7.

U.S. Patent Issued For Novare Surgical Systems Cygnet (R) Surgical Clamp; Novare Signs Multi-Year Supply Agreement With Boston Scientific; PR Newswire, pNA; Sep. 2, 2003.

Ou, CS et al.; *Total Laparoscopic Hysterectomy Using Multifunction Grasping, Coagulating, And Cutting Forceps*; Apr. 2004 J Laparoendosc Adv Surg Tech A.; 14 (2): 67-71; Department of Research and Development, Northwest Hospital and University of Washington School of Medicine, Seattle, Washington 98155, USA. cou@nwhsea.org.

Pavlov, IUV et al.; *Ultrasonic Technologies In Diagnosis And Treatment Of Patients With Surgical Diseases Of Lungs And Pleura*; 2003 Khirurgiia (Mosk).; (8): 30-4.

Petrakis, IE et al.; *Use Of The Ligasure Vessel Sealer In Total Abdominal Hysterectomy*; Jun. 2005 Int J Gynaecol Obstet.; 89 (3): 303-4. Epub Mar 2, 2005; Department of General Surgery, University General Hospital of Heraklion, University of Crete, Heraklion, Crete, Greece. petrakis@post.com.

*Quadripolar Cutting Forceps Introduced By Everest Medical*; Jan. 2000; Health Industry Today, v. 63, n. 1, pNA.

*Radiofrequency Energy Proven Effective Against Leading Cause Of Obstructive Sleep Apnea*; Sep. 14, 1998; Business Wire, p. 09140175.

Raestrup, H. et al.; *Dissection Technique—Is Ultrasound the Best Method?*; 2001 Kongressbd Dtsch Ges Chir Kongr.; 118: 69-70; Universitatsklinik Fur Allgemeine Chirurgie, Hoppe-Seyler-Strasse 3, 72076 Tubingen.

Robinson JL et al.; *Bipolar Diathermy*; Sep. 1974 Can J Surg.; 17 (5): 287-91.

Srisombut, C. et al.; *Laparoscopic Hysterectomy Using Laparosonic Coagulating Shears: Experience Of 15 Cases*; Aug. 2000 J Med Assoc Thai.; 83 (8): 915-20; Department of Obstetrics and Gynecology, Faculty of Medicine, Ramathibodi Hospital, Mahidol University, Bangkok, Thailand.

Stanojevic, D. et al.; *An Ultrasonic Scalpel For Laparoscopic Gynecologic Surgery*; May-Jun. 1998 Srp Arh Celok Lek.; 126 (5-6): 214-6; Narodni Front Department of Gynecology and Obstetrics, Dr. Dragisha Mishovitsh Medical Centre, Belgrade.

Sugi, K. et al.; *Use Of The Bipolar Vessel Sealing System In Lung Resection*; 2003 Jul. Kyobu Geka.; 56 (7): 551-4; Department of Clinical Research, National Sanyo Hospital, Ube, Japan.

Tajiri M. et al.; *Evaluation Of An Ultrasonic Cutting And Coagulating System (Harmonic Scalpel) For Performing A Segmental And Wedge Resection Of The Lung*; Dec. 1998 Kyobu Geka.; 51 (13): 1116-9; Department of Surgery, Kan to Rosai Hospital, Kawasaki, Japan.

Tamussino, K. et al.; *Electrosurgical Bipolar Vessel Sealing For Radical Abdominal Hysterectomy*; Feb. 2005 Gynecol Oncol.; 96 (2): 320-2;Department of Obstetrics and Gynecology, Medical University of Graz, Auenbruggerplatz 14, A-8036 Graz, Austria. Karl.tamussino@meduni-graz.at.

The Gynecare Versapoint; http://www.jnjgateway.com/home.jhtml?loc=USENG&page=viewContent &contentId=edea000100001747&parentId=fc0de00100000334; All contents copyright © Johnson & Johnson Gateway, LLC 2000-2005.

Timor-Tritsch IE et al.; *Transvaginal Ultrasound-Assisted Gynecologic Surgery: Evaluation Of A New Device To Improve Safety Of Intrauterine Surgery*; Oct. 2003 Am J Obstet Gynecol.; 189 (4): 1074-9; Department of Obstetrics and Gynecology, New York University School of Medicine, NY 10016, USA. ilan.timor@med.nyu.edu.

Tucker, RD et al.; *Bipolar Electrosurqical Sphincterotomy*; Gastrointest Endosc. Mar.-Apr. 1992; 38 (2): 113-7; Department of Pathology, University of Iowa Hospitals Clinics, Iowa City 52242.

Tucker, R.D. et al.; *Capacitive Coupled Stray Currents During Laparoscopic And Endoscopic Electrosurqical Procedures*; Jul.-Aug. 1992; Biomedical Instrumentation & Technology vol. 26, No. 4 p. 303-11;; USA.

*Valley Forge Scientific Corp.—Company Report*; Jan. 27, 1993; Investext, p. 1-1.

Valleylab Products—*Electrosurgical Forceps: The Surgeon's Choice For Quality And Precision*; http://www.valleylab.com/product/es/accessories/forceps_over.html; © 2005 valleylab.

Weyl, BP; *How To Increase The Proportion Of Vaginal Hysterectomies-Bipolar Coagulation*; 1999 Sep. Am J Obstet Gynecol.; 181 (3): 768.

Wilson, Fred; *Cool Tool, Hot New Application: Radiofrequency Energy Removes Head, Neck Tumors. (Dermatologic Surgery)*; Aug. 2003; Dermatology Times, v. 24, n. 8, p. 54.

Zhi, Xu-Ting et al.; *Management Of Gastroesophageal Reflux Disease: Medications, Surgery, Or Endoscopic Therapy? (Current Status And Trends)*; 2005; Journal of Long-Term Effects of Medical Implants v. 15 n. 4 2005. p. 375-388.

*Gyrus Medical: LP Scissors*; retrieved on Oct. 20, 2005 from website: http://www.gyrusgroup.com/medical/products_item.asp?id=11.

Gyrus Medical: Micro/Macro-Jaw Forceps; retrieved on Oct. 20, 2005 from website: http://www.gyrusgroup.com/medical/products_item.asp?id=13.

Gyrus Medical: Cutting Forceps; retrieved on Oct. 20, 2005 from website: http://www.gyrusgroup.com/medical/products_item.asp?id=7.

Gyrus Medical: Lyons TM Dissecting Forceps; retrieved on Oct. 20, 2005 from website: http://www.gyrusgroup.com/medical/products_item.asp?id=8.

Gyrus Medical: Seal TM Open Forceps; retrieved on Oct. 20, 2005 from website: http://www.gyrusgroup.com/medical/products_item.asp?id=15.

Valleylab Products—Ligasure TM Vessel Sealing System; retrieved on Oct. 20, 2005 from website: http://www.valleylab.com/product/vessel_seal/index.html © 2005 valleylab.

\* cited by examiner

METHOD AND APPARATUS FOR SURGICAL ELECTROCAUTERY

BACKGROUND OF THE INVENTION

1. Technical Field

The invention relates to medical devices. More particularly, the invention relates to a method and apparatus for surgical electrocautery.

2. Description of the Prior Art

Electrocauterization is the process of cauterizing, coagulation, and/or destroying tissue with electricity. A small probe with an electric current running through it is used to cauterize (burn or destroy) the tissue. The procedure is frequently used to divide tissue structures in a fashion which is hemostatic (seals blood vessels, thereby preventing bleeding). See, for example, Y. C. Jou, M. C. Cheng, J. H. Sheen, C. T. Lin, P. C. Chen, *Electrocauterization of bleeding points for percutaneous nephrolithotomy*, Urology 64(3):443-6 (September 2004). The use of electrocautery has been extremely beneficial for the performance of surgical procedures, such as hysterectomy (the surgical removal of the uterus), where relatively long spans of tissue must be sealed and divided to remove the organ. Experiments to date with a set or sets of single continuous electrode pairs running the length of a device's long jaws have resulted in inconsistent arterial sealing and tissue cauterization. These inconsistent outcomes are likely due to inconsistent electrode contact with the long (1-15 cm), complex tissue sheets. That is, while the electrodes and their backing surfaces are rigid, the tissue sheets are highly variable in their thickness and composition, given that the tissue sheets frequently contain arteries, veins, nerves, ligaments, lymphatics, etc.

To achieve sealing along the entire tissue length, the electrode or its backing surface must be conformable, but also must still be able to deliver adequate force to produce an adequate electrocautery seal. While a compressible material, such as a polymer or foam, can work, these materials do not transfer consistent force because the compressed regions of the material exert higher force than in those regions where tissue is thinner, and the material is less compressed.

One solution in addition to the incorporation of conformable electrodes is to create multiple electrodes, where each electrode may have a different sealing profile, either from an electric power or energy standpoints, or from a conformability standpoint; and/or electrodes with a conformal surface, either under the electrode or as a standoff to the sides of the electrodes. While this approach is promising, there is still more to do.

It would therefore be advantageous to provide a surgical electrocautery method and apparatus that achieves sealing along the entire tissue length, and that also is able to deliver adequate force to produce an effective electrocautery seal.

SUMMARY OF THE INVENTION

The invention provides a surgical electrocautery method and apparatus that achieves sealing along the entire tissue length, and that also is able to deliver adequate force to produce an effective electrocautery seal. One way to solve this problem is by using an incompressible fluid contained in sac positioned to support the one or more electrodes used for electrocauterization. The profile of the electrodes thus conforms to the tissue surface and thickness variations, while exerting an equal pressure along the entire length of the surface. Alternative embodiments of the invention comprise the use of various gels, either contained within a sac or in place and not contained within a sac; and various arrangements of springs and combinations of springs and fluid substrates upon which the electrodes are placed. The invention also contemplates the unique forming electrodes on the fluid filled sac itself, for example by sputtering, spraying, or dipped coating; as well as the use of various springs as conformance members and as conductors, i.e. electrodes.

DETAILED DESCRIPTION OF THE INVENTION

The invention provides a surgical electrocautery method and apparatus that achieves sealing along the entire tissue length, and that also is able to deliver adequate force to produce an effective electrocautery seal. One way to solve this problem is by using an incompressible fluid contained in sac positioned to support the one or more electrodes used for electrocauterization. The profile of the electrodes thus conforms to the tissue surface and thickness variations, while exerting an optimized pressure along the entire length of the surface. Alternative embodiments of the invention comprise the use of various gels, either contained within a sac or in place and not contained within a sac; and various arrangements of springs and combinations of springs and fluid substrates upon which the electrodes are placed. The invention also contemplates the unique forming electrodes on the fluid filled sac itself, for example by sputtering, spraying, or dipped coating; as well as the use of various springs as conformance members and as conductors, i.e. electrodes.

Figure 1:
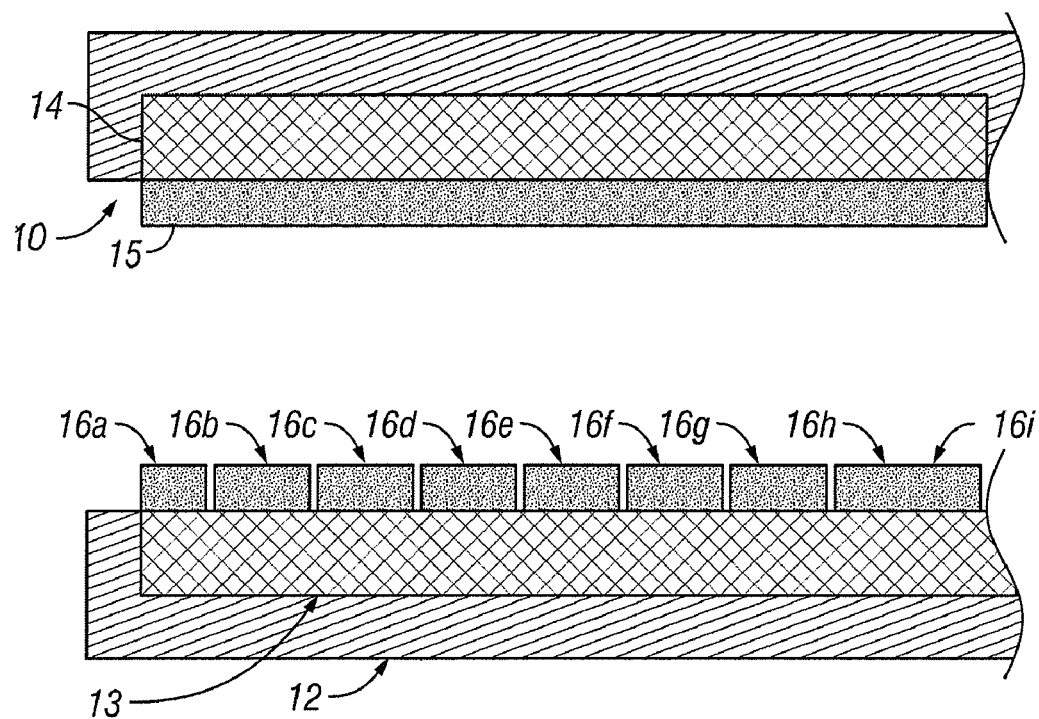
FIG. 1 is a side view of an electrocautery device according to a first embodiment of the invention.

FIG. 1 is a side view of an electrocautery device according to a first embodiment of the invention.

The invention may comprise a fluid filled sac. The fluid may comprise, for example, a liquid, such as saline or Ringer's solution, or another biocompatible liquid or gel. Biocompatibility is desired due to the potential for rupture of the liquid or gel-containing portion of the inventive sac. One or more electrodes are mounted to the liquid filled sac. The sac, or balloon, can either be pre-filled with liquid or gel, or filled once it has been delivered to the site at which the electrocautery (electrosealing) is to be performed. Thus, the amount of liquid or gel contained in the sac may be adjusted as desired for the application to which the device is put. The sac itself may be made from any biocompatible material, such as a surgical rubber or vinyl material, as is known in the art. The material should also be non-conductive and heat resistant. Further, the sac may be either a flexible, leak proof covering for a well formed within the jaws of an electrocautery device, or it may be a balloon-like sac that entirely contains the liquid or gel and that is attached to a jaw of the electrocautery device.

The device of FIG. 1 comprises a pair of jaws 10, 12, each of which comprises a rigid support member. The jaws are movable between a first, closed position for clamping a tissue therebetween for electrocautery and a second, open position. The manner for effecting this movement is not shown in the figures and is considered to be a matter of choice for the person skilled in the art.

At least one of the jaws comprises a liquid or gel filled sac 13, 14. In this embodiment, a single electrode 15 may be provided on either side of the device jaws, or a plurality of electrodes 16a-16i may be provided on one or both jaws of the device. In the case of individual electrodes, the electrodes may be of varying lengths and thicknesses. Further, the materials from which the electrodes are formed may be varied, all based on the sealing needs of the tissue in the specific region to be sealed.

FIG. 1 shows a first jaw comprising a liquid or gel filled sac having a plurality of electrodes attached thereto, with a second jaw comprising a single (or multiple) return electrode(s). Those skilled in the art will appreciate that a fluid filled sac may be provided on either or both jaws, or on just portions of one or both jaws. The sacs may be filled with a liquid, gel, small particles, compressed gas, or any combination thereof, although an incompressible fluid is presently preferred and a compressed gas would not be appropriate for many applications to which the device is intended to be put. Nonetheless, a compressed gas is contemplated as one medium for filling the sacs that is within the scope of the invention.

Key to the invention is that the electrodes overlay a conforming substrate which forms a portion of the jaw with which the electrode is associated. A liquid or gel filled sac allows liquid or gel to be displaced in regions beneath the electrodes that contact tissues that are thicker, for example, and thus fill in those regions of the sac that underlay tissue contacted by the electrodes that is thinner. Thus, thicker tissues push electrodes into the sac and thus force the liquid or gel to push the electrodes at or near the thinner tissue closer to the tissue at these locations. In this way, conformity of the electrodes to the tissue is achieved. This is advantageous not only during initial contact of the electrodes with the tissue to offset variations in the thickness of the tissue, but also as the process of cauterization proceeds and the thickness of the tissue is altered. That is, as the tissue is cauterized, some regions that are thicker may become thinner. Because the thickness profile of the tissue is altered in an unpredictable fashion by the cauterization process, the ability of the electrodes to conform with the tissue becomes an important factor in assuring even and complete cauterization across the span of tissue that is clamped between the jaws of the device for cauterization.

In other embodiments of the invention, the sac may be partitioned, based upon a profile of the tissue or electrodes. For example, the sac may have one portion that contains more liquid or gel and that thus presents those electrodes to the tissue somewhat more displaced from the jaw than electrodes associated with a portion of the sac that is less highly filled. This differential in liquid or gel contained in the sac partitions provides a profile to the electrodes that more nearly matches the thickness/thinness of the tissue, and yet allows for conformity of the electrodes within each region. That is, partitioning the sacs serves to both predispose the electrodes to a thinner or thicker tissue, while retaining the ability of the electrodes to conform to local variations in the tissue thickness.

Further, the partitions within the sac may be communicatively coupled to allow a restricted flow of liquid or gel therebetween. The restriction allows some redistribution of the liquid or gel between the sacs, and yet provides for a differing electrode profile at different regions along the length of the jaws.

An alternative embodiment that approximates the desired results uses a gel or foam material, or mechanical spring geometry either in one or more sacs or, in the case of a gel having more mechanical integrity, i.e. solidity, or as one or more stand-alone mounting materials that replaces the sac entirely and upon which the electrodes are disposed.

The sac material itself can constitute the electrode, as well as functioning to contain the incompressible fluid. In this embodiment of the invention, a thin coating of a conductive material or a coating filled with conductive material can be preferentially applied onto a portion of the surface of the sac that comes into contact with the tissue to be sealed. The conductive material can be applied by any known technique, such as sputtering, spraying, photolithography, or dipped coating. Further, the material can be patterned when applied, such that a plurality of electrodes may be formed, and where the electrodes each have a different shape, size, or other constitution, as desired. The leads necessary to connect the electrodes to a power source may be formed in this matter as well. This embodiment of the invention avoids the problems that may occur where the sac provides a conformal substrate for the electrodes, but the electrodes are formed of relatively rigid material that defeats the conformal nature of the sac. Electrodes that are formed integrally on the surface of the sac according to this embodiment of the invention are always in conformance with the surface of the tissue to which they are contacted because they are part of the sac itself.

In other embodiments of the invention, the conformal material contained within a sac may be a solid polymer based material which provide increased pressure on the thickest tissue, for example where the arteries are located. In these locations, it is necessary to provide the most sealing force and, therefore, the most energy must be transmitted through the device to the tissue. In the embodiment employing a polymer based material, the material may have a surface pattern that is provided to optimize conformity while maintaining adequate support for the tissue to hold the tissue intact after the tissue is cauterized, for such procedures as cutting or sectioning the tissue, the surface pattern may be formed by any of molding, cutting, patterning, and the like, and may provide any desired topological relief, such as a pattern of bumps, notches, projections, ridges, weaves, depressions, and the like. Further, such surface patterning is not limited to the poly based material, but may also be employed with sacs and other conformance members.

In this embodiment of the invention, a balanced set of material properties in the conformal material insures intimate contact with varying tissue thicknesses from less than 1 millimeter to 1 centimeter or more to insure uniform sealing of the tissue, and also to exert the highest pressure in the area where it is needed most, i.e. the thickest region of the tissue. In one embodiment of the invention, the balancing of types of conformal materials provided to provide a profile of pressure is accomplished by a hybrid of technologies, such as a combination of liquids, gels, solid polymers, and springs (see below). For example, the embodiment of the invention which contemplates compartments within the sac may comprise a different material in each sac, where those portions of the device that contact areas of the tissue, such as arteries, are provided with a portion of the sac that is filled with a material that provides greater pressure to the tissue. Alternatively, such portions of the tissue may be confronted by a spring, or a spring may underlies a portion of the sac in those regions where additional pressure must be provided. Further, the substrate upon which the sac is placed could be profiled such that the fluid within the sac is predisposed to exert greater pressure at certain regions of the sac where such additional pressure is desired.

Figure 2:
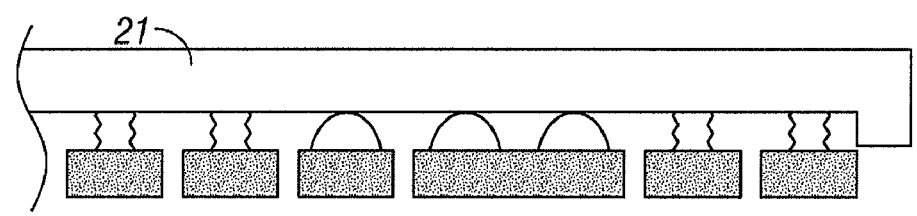
FIG. 2 is a side view of second embodiment of an electrocautery device according to the invention.
Figure 2:
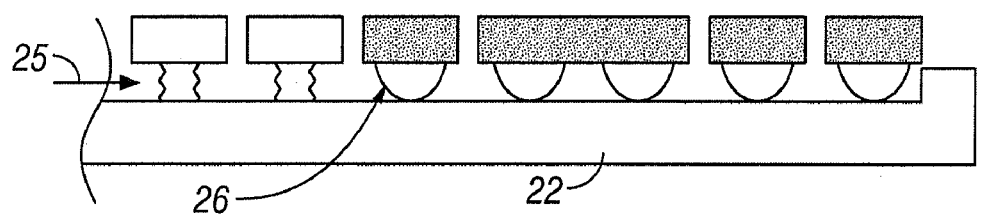

FIG. 2 is a side view of second embodiment of an electrocautery device according to the invention. This embodiment of the invention comprises a pair of jaws 21, 22, as above, and approximates the desired results mechanically by using springs, which may be, for example, coil springs 25 or leaf springs 26 (one example shown), or a combination thereof (as shown in FIG. 2), to effect compliance of the electrodes to the tissue. Those skilled in the art will appreciate that other types of springs may be used as well. However, this embodiment of the invention has similar limitations as that of an elastomer. The use of springs or elastomers may prove valuable in optimizing the distribution of force because the spring force is higher in areas where the springs are more compressed, such as in thicker tissue regions which are harder to cauterize. To allow control over this effect, springs with different tension may be provided across the span of the jaws, such that stronger or shorter springs are provided, for example, a regions of the tissue that are known to be thicker and that, thus, require more pressure and/or less travel to make proper contact with the tissue, while weaker springs or longer springs are provided, for example, in regions of the tissue that are known to be thinner and that, thus, require less pressure and/or more travel to make proper contact with the tissue.

Another embodiment of the invention is a hybrid of the invention shown in FIGS. 1 and 2, in which a liquid or gel filled sac is provided beneath a portion of the electrodes, while one or more springs may be provided beneath other electrodes. This embodiment of the invention may be applied to tissues that exhibit different properties along the region to be electrocauterized.

In an alternative embodiment of the springs, the springs may take the shape of a coil or they may be a loop spring or other spring. Further, the springs themselves may act as electrodes, as well as providing a resilient pressure bearing surface at the point in which the device contacts the tissue. In this embodiment of the invention, it is not necessary to provide separate electrodes. Further, the springs can be chosen for the amount of pressure they exert, such that a profile may be provided to the device that provides more pressure to those regions that which greater pressure is needed and less pressure at regions where less pressure is necessary. Further, the coil or spring electrodes can be formed from a material such as nitinol and may be used in conjunction with liquids, gels, or solid polymers to optimize the force and conformability balance of the device.

In another embodiment of the invention, the gel, liquid, polymer, or springs can compensatorily increase volume to maintain pressure as the tissue begins to electocauterize and thereby shrink. This embodiment of the invention maintains a somewhat constant pressure throughout the sealing cycle. The material used to effect the increase in volume of the sac or the material underlying the electrodes can be any known material that somewhat swells or stiffens during the electrocauterizing cycle as the material gets warmer, for example through conduction of heat from the tissue. Alternatively, a more complex system can be provided, as a dynamic pressure monitoring system with a compensation mechanism built into the fluid system of the sack, for example a thermistor could be provided that monitors the temperature of the tissue and that actuates a pump to increase the pressure in the sac by adding fluid to the sac. Alternatively, an end-point detection system as is used for electro-cautery could be coupled to the device to actuate a pump that compensates for shrinkage of the tissue by increasing the volume of the sac.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. An apparatus for surgical electrocautery, comprising:
   a pair of opposing jaws that are movable between an open position and a closed, clamping position;
   at least one electrode associated with one of said jaws, said at least one electrode being disposed between said jaws for contact with a tissue surface;
   at least one sac associated with one of said jaws and positioned between said jaw and said at least one electrode to support said at least one electrode;
   an incompressible fluid contained within said at least one sac, wherein said sac is prefilled with said incompressible fluid;
   wherein said at least one electrode exerts pressure upon said at least one sac when said jaws are moved to a closed, clamping position and said at least one electrode is brought into contact with said tissue surface, displacing said incompressible fluid within said at least one sac, wherein said at least one electrode conforms to said tissue surface while exerting an optimized pressure along an entire length of said tissue surface.

2. The apparatus of claim 1, said incompressible fluid comprising:
   a liquid comprising any of saline, Ringer's solution, a gel material, and another biocompatible liquid.

3. The apparatus of claim 1, wherein said at least one electrode is mounted to said at least one sac.

4. The apparatus of claim 1, wherein said at least one sac is made from a biocompatible material.

5. The apparatus of claim 1, at least one of said jaws comprising a plurality of electrodes.

6. The apparatus of claim 1, wherein at least one sac is provided on either or both jaws, or on portions of one or both jaws.

7. The apparatus of claim 1, wherein said at least one electrode is formed on a surface of said sac.

8. A method for effecting surgical electrocautery, comprising the steps of:
   providing a device having a pair of opposing jaws that are movable between an open position and a closed, clamping position;
   associating at least one electrode with one of said jaws, said at least one electrode being disposed between said jaws for contact with a tissue surface;
   associating at least one sac with one of said jaws and positioned between said jaw and said at least one electrode to support said at least one electrode;
   containing an incompressible fluid contained within said at least one sac, wherein said sac is prefilled with said incompressible fluid;
   wherein said at least one electrode exerts pressure upon said at least one sac when said jaws are moved to a closed, clamping position and said at least one electrode is brought into contact with said tissue surface, displacing said fluid within said at least one sac, wherein said at least one electrode conforms to said tissue surface while exerting an equal pressure along an entire length of said tissue surface.

9. An apparatus for surgical electrocautery, comprising:
   a pair of opposing jaws that are movable between an open position and a closed, clamping position;
   at least one electrode associated with one of said jaws, at least one electrode being disposed between said jaws for contact with a tissue surface;
   at least one conformance member associated with one of said jaws, positioned between said jaw and said at least one electrode to support said at least one electrode;
   wherein said at least one electrode exerts pressure upon said at least one conformance member when said jaw is moved to a closed, clamping position and said at least one electrode is brought into contact with said tissue surface, and wherein said at least one electrode conforms to said tissue surface while exerting an optimized pressure along an entire length of said tissue surface;

wherein said conformance member comprises at least one sac associated with one of said jaws, positioned between said jaw and said at least one electrode to support said at least one electrode; and an incompressible fluid contained within said at least one sac, wherein said sac is prefilled with said incompressible fluid.

10. The apparatus of claim 9, wherein said at least one electrode is formed on the surface of said sac.

11. The apparatus of claim 9, wherein said conformance member comprises a resilient member underlying said at least one sac.

12. The apparatus of claim 9, wherein said conformance member compensatorily increases in volume to maintain pressure on tissue as said tissue electrocauterizes and shrinks.

13. An apparatus for surgical electrocautery, comprising:

a pair of opposing jaws that are movable between an open position and a closed, clamping position;

at least one electrode associated with one of said jaws, said at least one electrode being disposed between said jaws for contact with a tissue surface;

at least one sac associated with one of said jaws and positioned between said jaw and said at least one electrode to support said at least one electrode, said sac comprising at least one partition defining at least two sac portions;

an incompressible fluid contained within each sac portion of said at least one sac, wherein said sac is prefilled with said incompressible fluid;

wherein said at least one electrode exerts pressure upon said at least one sac when said jaws are moved to a closed, clamping position and said at least one electrode is brought into contact with said tissue surface, displacing said incompressible fluid within said at least one sac, wherein said at least one electrode conforms to said tissue surface while exerting an optimized pressure along an entire length of said tissue surface.

14. The apparatus of claim 13, wherein said at least one partition establishes a communicative fluid coupling between said at least two sac portions.

* * * * *